United States Patent [19]

Hsu

[11] Patent Number: 4,652,526

[45] Date of Patent: Mar. 24, 1987

[54] ETHANOL-PRODUCING MUTANTS OF CLOSTRIDIUM THERMOSACCHAROLYTICUM

[75] Inventor: Edward J. Hsu, Kansas City, Mo.

[73] Assignee: The Curators of the University of Missouri, Columbia, Mo.

[21] Appl. No.: 559,208

[22] Filed: Dec. 8, 1983

Related U.S. Application Data

[63] Continuation-in-part of Ser. No. 288,059, Jul. 29, 1981, abandoned.

[51] Int. Cl.$^4$ .................. C12N 1/20; C12N 15/00; C12P 7/06; C12R 1/145
[52] U.S. Cl. ........................... 435/253; 435/172.1; 435/161; 435/842
[58] Field of Search ............ 435/161, 162, 163, 165, 435/253, 801, 842, 172.1

[56] References Cited

U.S. PATENT DOCUMENTS 4,292,406 9/1981 Ljungdahl et al. ............ 435/42
4,349,628 9/1982 English et al. ................ 435/161

OTHER PUBLICATIONS

Hsu, *Spore Research*, ed. Gould and Wolf, Academic Press, 400–418, (1976).
Hoffman, *Spores VII*, American Society for Microbiology, Washington, D.C., 312–318, (1978).
Hsu et al, J. Bacteriol., 102(2): 369–376, (1970).
Herrero et al, Applied Environ. Microbiol., 40(3): 571–577, (1980).
Avgerinos et al, *Advances in Biotechnology*, vol. II, Pergamon Press, New York, 119–124, (1981).
Wang et al, 3rd Annual Biomass Energy Systems Conference Proceedings, Colorado School of Mines, Golden, Colorado, Jun. 5–7, 1979, 61–67.
Hsu et al, J. Bacteriol., 97(3): 1511–1512, (1969).
Hsu et al, Applied Microbiol., 18(5): 958–960, (1969).
Jones et al, Applied Environ. Microbiol., 43(6): 1434–1439, (1982).

*Primary Examiner*—Esther M. Kepplinger
*Attorney, Agent, or Firm*—Tilton, Fallon, Lungmus & Chestnut

[57] ABSTRACT

Several mutant *Clostridium thermosaccharolyticum* strains, ATCC No. 31907, 31908 and 31909, which are elongated and non-dividing produce ethanol.

6 Claims, No Drawings

ETHANOL-PRODUCING MUTANTS OF *CLOSTRIDIUM THERMOSACCHAROLYTICUM*

RELATED APPLICATION

This application is a continuation-in-part of copending application Ser. No. 288,059, filed July 29, 1981 now abandoned.

BACKGROUND OF INVENTION

The field of the invention is the fermentation of biomass substrates with thermophilic anaerobes to produce alcohols, especially ethanol. More particularly, the invention is concerned with novel mutants of *Clostridium thermosaccharolyticum* which are capable of producing higher yields of ethanol.

Lee and Ordal[1], in 1967, reported that *C. thermosaccharolyticum* produced ethanol as one soluble end product of the dead cells of a fermentation by glucose-grown cells in Warburg flasks at 56° C. More recently, Ljungdahl and Wiegel[2] have reported on ethanol fermentations using strains of anaerobic thermophilic bacteria at the 27th IUPAC Congress in Helsinki, 1979. Some of the strains were identified as *Clostridium thermohydrosulfuricum*, previously isolated only from extraction juices obtained in an Austrian sugar beet factory. A second strain of anaerobic thermophilic bacterium was also identified with a proposed name of *Thermoanaerobium ethanolicum*. This bacterium has a temperature range of 37° to 78° C. and was isolated from the mud samples taken from hot springs. It differs from *C. thermohydrosulfuricum* in that it does not form spores and produces, during fermentations, almost 2 moles of ethanol and carbon dioxide per mol of fermented glucose with lactate, acetate, and $H_2$ as minor products.

A type of vacuum fermentation system, including a cell recycling procedure, for the production of ethanol has been described by Cysewzki and Wilke[3]. Their studies were conducted using a yeast, *Saccharomyces cerevisiae* (ATCC No. 4126), at a fermentation temperature of 35° C. A 10% glucose feed was employed and a cell density of 50 g dry wt/liter was obtained in an atmospheric-cell recycle fermentation which produced a fermentor ethanol productivity of 29.0 g/liter-hr. The vacuum fermentor eliminated ethanol inhibition by boiling away ethanol from the fermenting beer as it was formed. At a total pressure of 50 mm Hg using a 33.4% glucose feed, ethanol productivities of 82 and 40 g/liter-hr were achieved with the vacuum system with and without cell recycle, respectively. Fermentor ethanol productivities were thus increased as much as twelvefold over conventional continuous fermentation. However, in order to maintain a viable yeast culture in the vacuum fermentor, a bleed of fermented broth had to be continuously withdrawn to remove nonvolatile inhibiting compounds. It was also found necessary to sparge the vacuum fermentor with pure oxygen periodically to satisfy the trace oxygen requirement of the fermenting yeast.

Dr. Edward J. Hsu, (the inventor named herein) and his associates have been working with *Clostridium thermosaccarolyticum* (National Canners Association strain 3814)[4]. This work stemed from the initial observation that this species of Clostridia is highly resistant to heat at normal sterilization temperatures. Lee and Ordal[1] earlier had found ethanol as an end product from the fermentation of such cells.

In this work leading up to the present invention, involved other developments relating to the use of anaerobic thermophiles in ethanol production. These developments are described below in abbreviated form:

(1) One development was the continuous cultivation of the oxygen-sensitive clostridia to induce a morphological change such as elongation and/or sporulation.[4,5]

(2) A further development was the finding that metabolic change occured as morphological changes proceeded.[6] Little or no ethanol was apparent, until the cells elongated and developed into sporangia.

(3) Still another important finding was that of the conversion of acetate to ethanol in cells undergoing elongation and sporulation.[6,7] De-repressed levels (78 times) of ethanol dehydrogenase, and higher levels of NADPH were also found in the elongating cells.

(4) It has also been determined that elongating cells producing predominate amounts of ethanol and dehydrogenase are essentially non-dividing cells. These cells can be arrested at this stage, so that sporulation does not proceed;[7] in fact, highly synchronized cultures can be obtained by an interruption in cell division, and sporogenesis.[8] This last discovery implies that sporulation per se is not essential to ethanol production, and that the change in cell length is perhaps responsible for the metabolic shift.

Each of these four developments described above had disadvantages and were found insufficient to establish a viable ethanol production system. It was found that the continuous culture to induce morphological change required that the organism be cultivated at an extremely low concentration (density), therefore, relatively low concentration of ethanol was produced.

There were also some disadvantages found in the second development relating to the shifting metabolism, these were: (1) little or no ethanol was produced by the short cells; (2) the amount of ethanol produced became significant only after the majority of cells started to elongate; and (3) the amount of ethanol became predominate only for a very short period of time, i.e. only by cells that were successfully converting to sporangia.

In the third development above, the cultivation technique to de-repress levels of ethanol dehydrogenase, it was found that the ethanol concentration was dependent on synchrony of the population, which was difficult to maintain.

In the fourth development, a disadvantage observed was that the method was mostly unsuccessful due to unstable physiological conditions. Harvesting such an organism would be extremely difficult and probably not economically feasible.

SUMMARY OF INVENTION

The present invention involves the development of mutated strains of *C. thermosaccharolyticum* which are genetically adapted for phenotypic expression of greatly increased yields of ethanol from selected carbohydrate substrates. The genetic mutation is characterized by cell elongation without cell division of at least 10 to 20 times (10 to 20) the cell length prior to elongation. This elongation is observed in a medium promoting cell elongation as induced prior to cell sporulation. The mutated hyper-elongating cells are also preferably non-sporulating, that is, by not forming complete sporangia. Further, the mutant strains may also or alternatively to being non-sporulating have the characteristic of forming partial septations, as distinguished from the complete septations which form in the normal process of cell division after a lesser degree of elongation (viz. 4 to 5×).

Three mutant strains have been developed which are representative of the class of elongating, non-dividing mutants which produce the increased ethanol yields. All of these are capable of induced elongation of 10 to 20× or more without cell division. One of the mutants selected further demonstrates the genetic characteristic of being non-sporulating under sporulation inducing conditions. Another strain represents selection for the additional genetic characteristic of forming only partial septations under conditions inducing cell elongation and septum formation.

The three mutants referred to above have been deposited with the American Type Culture Collection (ATCC) and are identified as follows:

(1) *C. thermosaccharolyticum* (elongating, non-dividing) Strain designation (end-126)-ATCC accession No. 31907, (2) *C. thermosaccharolyticum* (elongated, non-dividing, asporogenic), Strain designation (asp-323)-ATCC accession No. 31908; and (3) *C. thermosaccharolyticum* (elongating, non-dividing, partially septating), Strain designation (eps-427) ATCC accession No. 31909.

MORE DETAILED DESCRIPTION

The procedures for mutating and selecting the ethanol-producing mutants of this invention will now be described in detail.

The mutant forms of organism desired for this application are ones that are characterized as being hyper-elongated without cell division, and non-sporulating and/or partially septating mutants. These genetic characteristics are obtained as follows:

Induction and detection of non-division mutants. The hyper-elongating cells are derived from the wild type *Clostridium thermosaccharolyticum* (ATCC 7956) by the following procedure: The parent strain is incubated into a glucose broth (2 g/l for 8 h at 60° C. or until ⅔ of maximum yield is reached. These cells are then diluted with fresh glucose medium to the density of $1 \times 10^6$ cells per ml and then filtered rapidly on 47 mm membrane filter (pore size 45 um). After being washed on the filter with 5 to 10 ml of Tris-maleic (TM) (each component at 0.05 m and adjusted to pH 6.0 with NaOH), the cells are resuspended by placing the membrane in an amount of TM buffer equal to original culture volume. The filter membrane is then removed, and N-methyl-N'-nitrosoguanidine (NTG) is added directly to the cell suspension to give a final concentration of 100 ug/ml (100 mg/l). After incubation for 30 minutes, a 1.0 ml sample is filtered again on the membrane filter, washed with 5 ml of cold basal medium, and resuspended in 10 ml of basal medium. The second suspension is then serial diluted and spread on (1) glucose plates (2 mg/ml or 2g/l). Colonies of survivors from NTG treatment are replica plated on (2) lyxose+3-0-$CH_3$-glucose (2 mg/ml or 2g/l each)
(3) glucose+2-deoxyglucose plates (2 mg/ml or 2 g/l each) which are incubated at 60° C. for 12 h to 14 h to permit cell growth.

Isolates showing elongated cells (10–20×) on one of the three plates are scored as non-dividing cells. (These are detected directly under a 400× phase contrast microscope and confirmed again in cell suspension at 1000×.) The ATCC deposited strain No. 31907 is representative.

Non-sporulating mutants. Following the procedures described above for the induction and detection of the three classes of mutants, these mutants are further separated to identify and isolate ethanol resistant strains. The procedures used are substantially identical to those described above except that the colonies of survivors from NTG treatment are replica plated on:

(1) α-$CH_3$-glucoside (2 mg/ml or 2 g/l) Ex. II
(2) α-$CH_3$-glucoside+glucose (2 mg/ml or 2 g/l each) Ex. I & II
(3) β-$CH_3$-glucoside (2 mg/ml or 2 g/l) Ex. II
(4) β-$CH_3$-glucoside+glucose (2 mg/ml or 2 g/l each) Ex. I & II Isolates showing mature refractile spores are still identical to the wild type but anything that shows cells at immature stages, such as elongated cells (10–20×) with swollen heads are scored as non-sporulating mutants. The plate media employed are ones tending to induce cell elongation and sporulation. For a more complete discussion of the carbohydrates (carbon sources) used in such media see Hsu et al, *Appl. Microbiol.* (1969)[5]. The comparism between mature spores, which have light-reflecting white centers and cells with end enlargement which did not form spores is shown in FIG. 1 (p. 959) of the cited Hsu et al publication. The ATCC deposited strain No. 31908 is representative.

Selection may also be made for the characteristic of partial septation. The partial septation characteristic as distinguished from full septations which precede cell division is illustrated in Hsu (1976). (See FIGS. 4A, 4B (p. 231), FIGS. 8A, 8B (pp. 234–235).) The ATCC deposited strain No. 31909 is representative.

The above-identified mutant strains of *Clostridium thermosaccharolyticum* referred to by the designations (1) end-126 and ATCC No. 31907; (2) esp-323 and ATCC no. 31908; and (3) esp-427 and ATCC 31909 were deposited with the American Type Culture Collection, 12301 Parklawn Drive, Rockville, Md. 20852, on June 8, 1981. These mutant strains have the morphological characteristics described above.

Mutant forms of the thermophilic anaerobe *C. thermosaccharolyticum* produced according to the teachings herein are found to be stable, distinct organisms characterized by differentiating from the wild state by being hyper-elongating and non-dividing, and also non-sporulating and/or partially septated in character. These strains are found to be far more effective at producing ethanol and at the same time are far more tolerant to ethanol because of their decreased surface to volume ratio than any organisms presently known to exist in natural state. The organisms are in fact resistant to ethanol up to concentrations of approximately 6 to 10% of the culture broth. These organisms can grow efficiently within the temperature range of 55° C. to 70° C.

The cell mass of mutated strains may be produced using a recycle and vacuum system as described in Cysewski et al (1977)[3]. The majority of cells employed should demonstrate a very pronounced degree of elongation throughout the first 10–15 hours of continuous cultivation. Many of the cells should be approaching vegetative length of 15–20 times that of the short vegetative cells which predominated in the batch cultures or semi-batch cultures. An automatic collector may be attached to the growth vessel to receive the ethanol producing cells and they can be converted to a 70 ml culture, every hour, that contains an optimum concentration of the carbon sources for maximum ethanol production.

It is also possible to operate a chemostat or recycle system at higher dilution rates approaching maximum growth rate. A continuous flow cell can be connected to a spectrophotometer, which in turn regulates the flow rate of the reservoir. This can effectively convert the chemostat into a turbidostat without the risk of any deterioration into a batch culture. The principle of maximizing the number of ethanol producing cells at the fastest possible dilution rate, therefore, resembles the procedures for single cell protein production, except that the steady state concentration of the limiting carbon source must be sufficiently below saturation point (4.6 g/l) to permit morphological change. These active ethanol producing cells can then be introduced into batch cultures containing 0.4–50.0 g/l of the carbon source, every hour, so that the continuous culture can be operated at a high turn-over rate without the disadvantages of a slow restricted rate.

A high vacuum continuous culture system can also be used. This embodiment incorporates the additional advantage of vacuum fermentation. Since the organisms used are strictly anaerobic such vacuum fermentation is possible. In such a system, at higher substrate concentrations and higher ethanol concentrations, the strong inhibitory effect of the ethanol is greatly relieved both inside the growth chamber and in subsequent batch cultures, if such are utilized. The vacuum apparatus effectively draws off the ethanol as fast as it is produced and thereby reduces the inhibitory effect of the ethanol to the organism which produces the ethanol.

BIBLIOGRAPHY

1. Lee, C. K. and Ordal, Z. J. 1967. Regulatory Effect of Pyruvate on the Glucose Metabolism of *Clostridium thermosaccharolyticum*. J. Bacteriol. 94 (1): 530–536.
2. Ljungdahl, L. G.; Wiegel, J. and Rawson, J. R. 1979. Isolation from Soil and Properties of the Extreme Thermophile *Clostridium thermohydrosulfuricum*. J. Bacteriol. 139(3): 800–810.
3. Cysewski, G. R. and Wilke, C. R. 1977. Rapid Ethanol Fermentations Using Vacuum and Cell Recycle. Biotechnology and Bioengineering. XIX: 1125–1143.
4. Hsu, E. J. and Ordal, Z. J. 1968. Sporulation of *Clostridium thermosaccharolyticum* Under Conditions of Restricted Growth. J. Bacteriol. 97(3): 1511–1512.
5. Hsu, E. J. and Ordal, Z. J. 1969. Sporulation of *Clostridium thermosaccharolyticum*. Applied Microbiol. 18(5): 958–960.
6. Hsu, E. J. and Ordal, Z. J. 1970. Comparative Metabolism of Vegetative and Sporulating Cultures of *Clostridium thermosaccharolyticum*. J. Bacteriol. 102(2): 369–376.
7. Hsu, E. J. 1976. Synchronous Elongation of *Clostridium thermosaccharolyticum* and Its Relation to State I of Sporulation. In "Spore Research" (ed. G. W. Gould and J. Wolf), p. 223–242, Academic Press, London.
8. Hoffman, J. W., E. K. Chang, and E. J. Hsu, 1978. An Interruption in Cell Division by Catabolite Dilution Producing Synchronous Growth of *Clostridium thermosaccharolyticum*. In Spores VII, pp. 312–318. American Society for Microbiology, Washington, D.C.

I claim:

1. Mutants of *Clostridium thermosaccharolyticum* genetically adapted for producing ethanol, said mutants being characterized by elongating at least 10 to 20 times without cell division when plated on a medium selected from the group consisting of (1) a mixture of lyxose and 3-O-CH$_3$ glucose in proportions of 2 milligrams per milliliter of each, and (2) a mixture of glucose and 2-deoxyglucose in proportions of 2 milligrams per milliliter of each, said mutants being in the form of biologically pure cultures.

2. Mutants according to claim 1 which are further characterized by non-sporulation when plated on a medium selected from the group consisting of (1) $\alpha$-CH$_3$-glucoside and (2) $\beta$-CH$_3$-glucoside in the proportions of 2 milligrams per milliliter.

3. Mutants according to claim 1 which are further characterized by forming partial septations when plated as described in claim 1.

4. Mutants of *Clostridium thermosaccharolyticum* having the elongating and non-dividing characteristics of the mutant strain identified by ATCC accession No. 31907, said mutants being genetically adapted for producing ethanol and being in the form of biologically pure cultures.

5. Mutants of *Clostridium thermosaccharolyticum* having the elongating, non-dividing and non-sporulating characteristics of the strain dientified by ATCC Accession No. 31908, said mutants being genetically adapted for producing ethanol and being in the form of biologically pure cultures.

6. Mutants of *Clostridium thermosaccharolyticum* having the elongating, non-dividing, and partial septating characteristics of the strain identified by ATCC Accession No. 31909, said mutants being genetically adapted for producing ethanol and being in the form of biologically pure cultures.